US00PP34537P3

(12) United States Plant Patent
Boches et al.

(10) Patent No.: US PP34,537 P3
(45) Date of Patent: Sep. 6, 2022

(54) BLUEBERRY PLANT NAMED 'FCM14-031'

(50) Latin Name: ***Vaccinium corymbosum* hybrid**
Varietal Denomination: FCM14-031

(71) Applicant: Fall Creek Farm and Nursery Inc., Lowell, OR (US)

(72) Inventors: Peter Stefan Boches, Hilo, HI (US); Antonio A. Alamo Bermudo, Seville (ES)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 0 days.

(21) Appl. No.: 17/498,055

(22) Filed: Oct. 11, 2021

(65) Prior Publication Data

US 2022/0117127 P1 Apr. 14, 2022

Related U.S. Application Data

(60) Provisional application No. 63/090,402, filed on Oct. 12, 2020.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

(56) References Cited

U.S. PATENT DOCUMENTS

PP29,125 P3 3/2018 Brazelton

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

The new blueberry plant variety 'FCM14-031' is provided. 'FCM14-031' is a commercial variety intended for the hand harvest fresh market. The new blueberry plant originated from a cross of 'FL00-180' (female parent, not patented) and 'FL01-06' (male parent, not patented). 'FCM14-031' forms round medium vigor bush growth habit, displays well branched habit, produces early to mid-season fruit, and exhibits fruit that is large with a flat bottom and an open upright calyx that has a mildly aromatic flavor that has a balance between sweet and acidity.

5 Drawing Sheets

Latin name of the genus and species:
Genus—*Vaccinium.*
Species—*corymbosum* hybrid.
Variety denomination: The new blueberry plant claimed is of the variety denominated 'FCM14-031'.

STATEMENT REGARDING FEDERALLY-SPONSORED RESEARCH AND DEVELOPMENT

None.

BACKGROUND OF THE INVENTION

The present invention relates to the discovery of a new and distinct cultivar of southern highbush blueberry (*Vaccinium corymbosum* L. hybrid) plant, referred to as 'FCM14-031', as herein described and illustrated.
Pedigree and History:

The new blueberry plant originated from a cross of 'FL00-180' (female parent, not patented) and 'FL01-06' (pollen parent, not patented).

The cross that produced 'FCM14-031' (denominated by the cross code 'X12-078') was made in Lowell, Oreg. in 2012. The seeds were then germinated in Lowell, Oreg., and young seedlings were shipped and transplanted for evaluation to Tala, Jalisco Mexico.

The seedling family was planted in Tala, Jalisco Mexico in May 2013, then one plant was selected and propagated by softwood cuttings for further clonal evaluation for fruit production and quality in 2014. The growing region of Jalisco, Mexico where 'FCM14-031' was originally selected is located at 20° 39'40" N, 103° 4'35" O, 1310 meters above sea level. In this region, temperatures range from 43° F. to 92° F. and is rarely below 36° F. and day lengths only vary from between 10.8 hours in December to 13.2 hours in June. Under these conditions, many traditional low-chill blueberry varieties (developed in latitudes 25°-35°) do not produce flower buds or flowers. In the case of blueberry varieties that do flower under these conditions, the flowers are produced primarily on the current season's growth that is often referred to as a primocane in the blueberry industry. The primocane inflorescences tend to be very elongated in form compared to the inflorescence produced at higher latitudes from dormant buds, and the fruit often does not abscise well from the pedicel, resulting in a large picking scar which greatly limits shelf life. The blueberry industry in this area is dominated by the variety 'Biloxi'. 'Biloxi' is one of the few traditional low chill varieties that grows well and produces fruit with a good picking scar in this growing environment. However, 'Biloxi' often produces an excessive proportion of small, unmarketable fruit.

After being selected in 2014, 'FCM14-031' was propagated by softwood cuttings and plots of 5 plant plot were established in Tala, Jalisco Mexico (near Guadalajara). The five plant plots were evaluated for fruit quality and yield in comparison to the standard varieties 'Biloxi' (not patented) and 'FCM12-131' (U.S. Plant Pat. No. 29,125) beginning in 2015. After five harvest seasons of evaluation, the yield and fruit quality of 'FCM14-031' were deemed sufficiently good to warrant launching it as a commercial variety.

'FCM14-031' was selected because of the high fruit quality, adaptability to storage, and a round medium vigor bush. 'FCM14-031' was also selected for use in an evergreen production system in areas where zero effective chilling hours may be accumulated.

'FCM14-031' has been found to undergo asexual propagation in Tala, Jalisco Mexico by in vitro propagation and soft wood cuttings. Asexual propagation techniques in Tala, Jalisco Mexico, such as in vitro propagation, have shown that the characteristics of the new variety are homogenous, stable, and strictly transmissible by such asexual propagation from one generation to another. Accordingly, the new variety undergoes asexual propagation in a true-to-type manner.

SUMMARY OF THE INVENTION

'FCM14-031' is a commercial variety intended for the hand harvest fresh market. 'FCM14-031' is distinguished by its high fruit quality and a round medium vigor bush. It was found that 'FCM14-031':

(1) forms round medium vigor bush growth habit,
(2) displays well branched habit,
(3) produces early to mid-season fruit, and
(4) exhibits fruit that is large with a flat bottom and an open upright calyx that has a mildly aromatic flavor that has a balance between sweet and acidity.

The new variety of the present invention can readily be distinguished from its ancestors. More specifically, the 'FL00-180' variety (i.e., seed parent) displays an upright bush habit, whereas the new variety displays a round bush shape habit that is more vigorous than the female parent. In addition, the new variety produces earlier and higher volumes of fruit compared to the 'FL00-180' variety. The 'FL01-06' variety (i.e., pollen parent) produces lighter, more acidic, and smaller fruit compared to the new variety and displays a low vigor bush, whereas the new variety displays a medium vigor bush.

The new variety can also be distinguished from other similar varieties. For instance, the new variety of the present invention can readily be distinguished from the 'Biloxi' variety as the new cultivar consistently produces firmer fruit than the 'Biloxi' variety.

BRIEF DESCRIPTION OF THE DRAWINGS

The accompanying photographic illustrations show typical specimens in full color of the foliage and fruit of three-years old plants the new variety 'FCM14-031'. The colors are as nearly true as is reasonably possible in a color representation of this type.

DETAILED BOTANICAL DESCRIPTION

Figure 1:
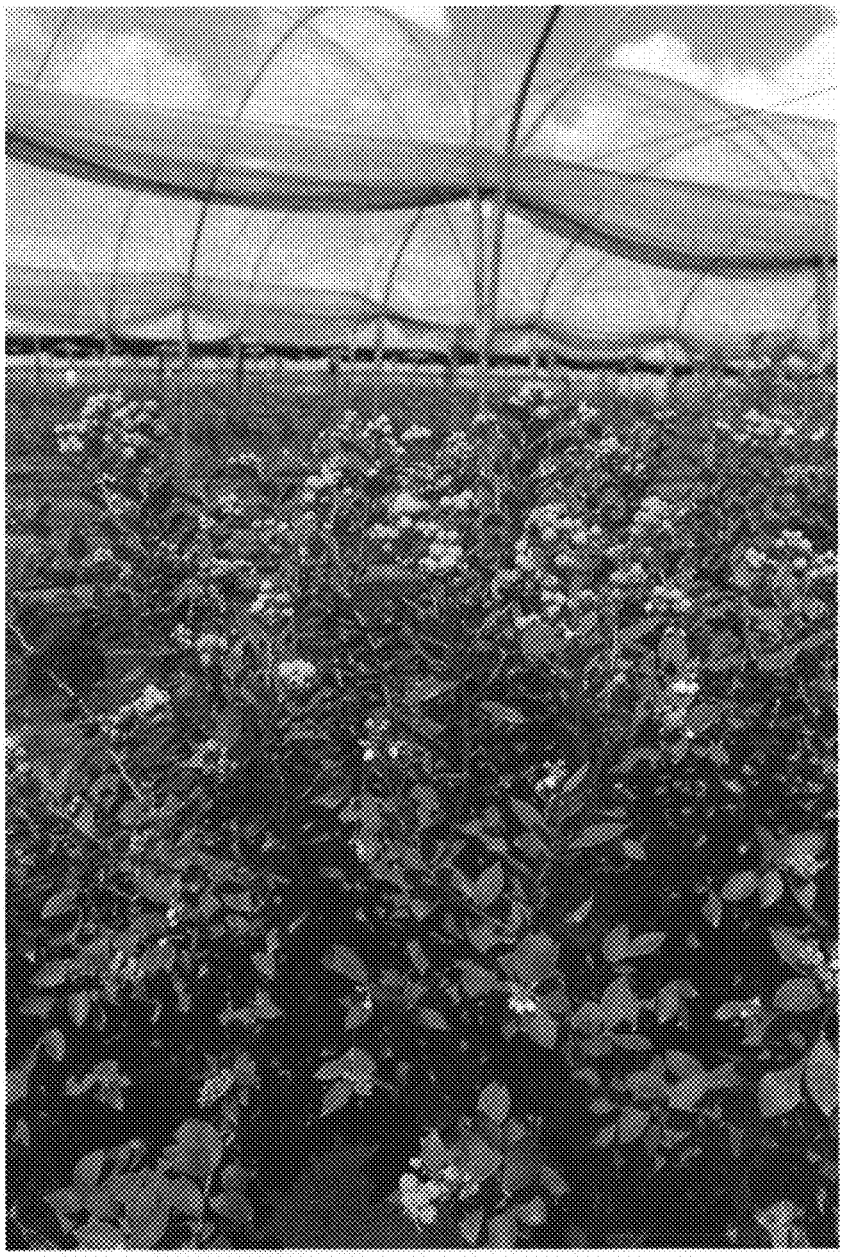
FIG. 1—depicts a mature plant of 'FCM14-031' grown in Tala, Jalisco, Mexico and photographed on Sep. 25, 2018.
Figure 2:
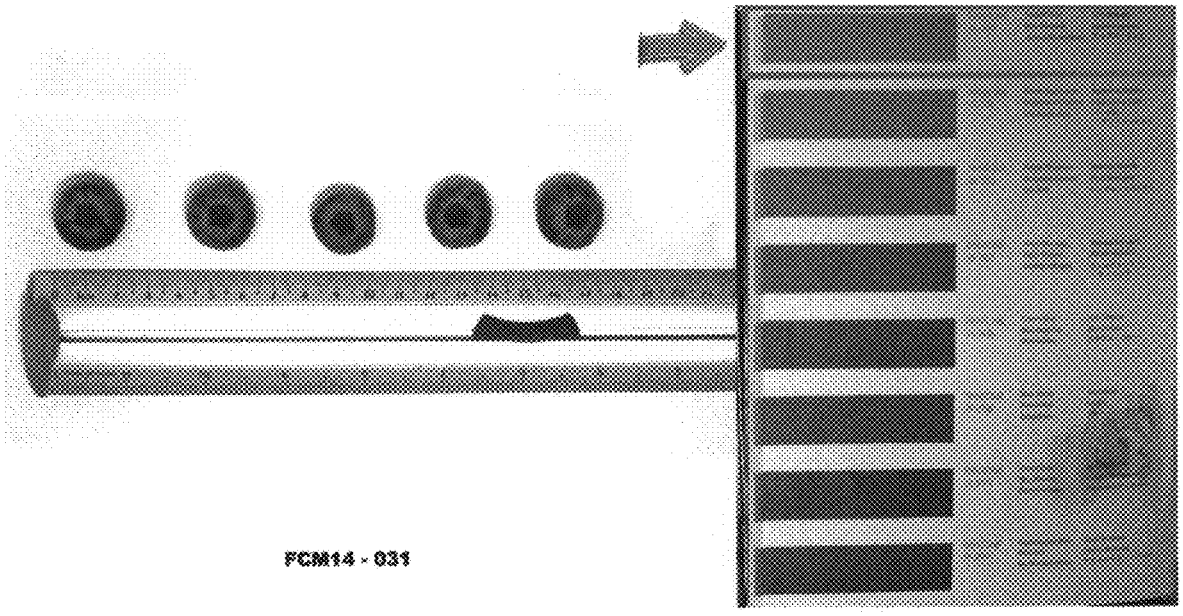
FIG. 2—depicts mature fruit of 'FCM14-031' grown in Tala, Jalisco, Mexico photographed on Sep. 25, 2018.
Figure 3:
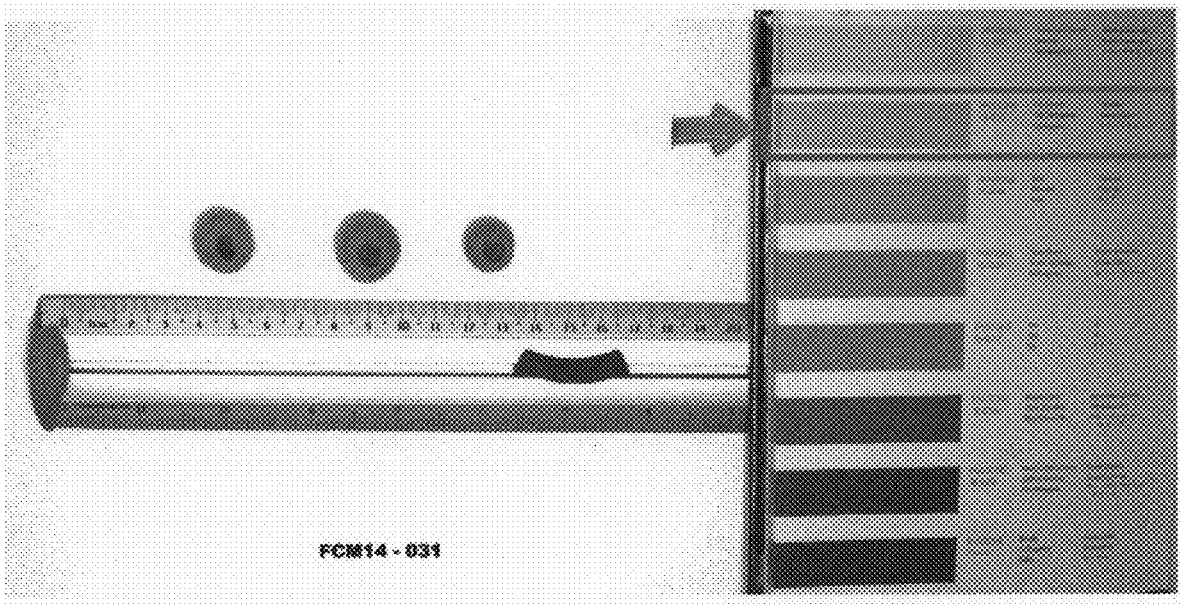
FIG. 3—depicts immature fruit of 'FCM14-031' grown in Tala, Jalisco, Mexico and photographed on Sep. 25, 2018.
Figure 4:
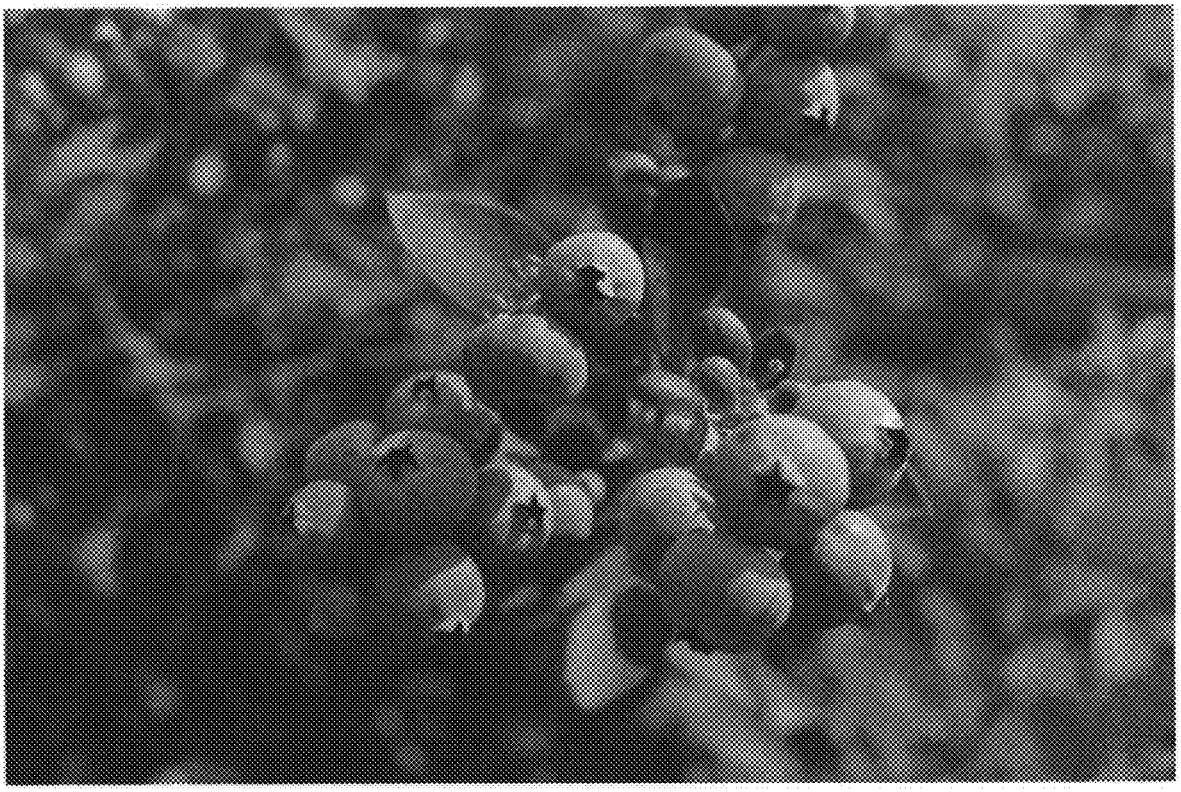
FIG. 4—depicts a fruit cluster of 'FCM14-031' grown in Tala, Jalisco, Mexico and photographed on Sep. 25, 2018.
Figure 5:
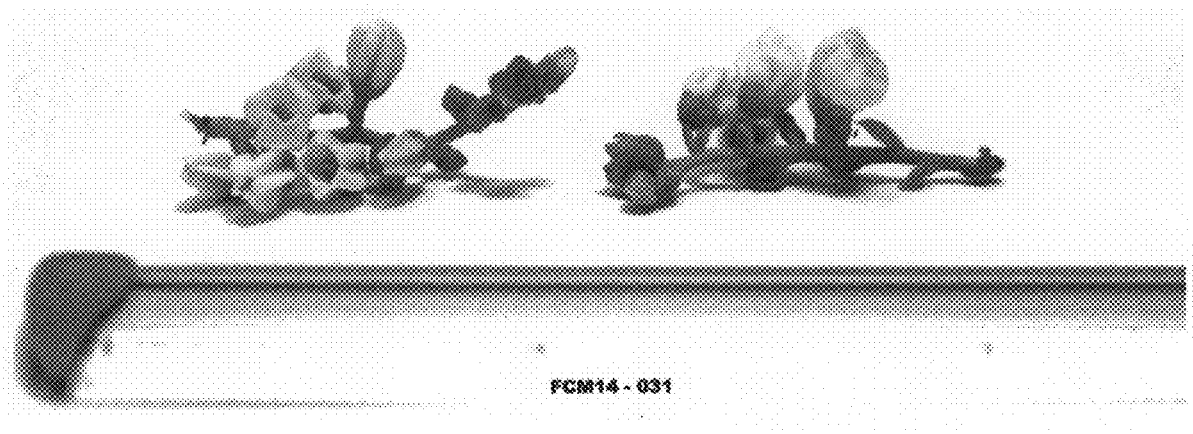
FIG. 5—depicts flowers of 'FCM14-031' grown in Tala, Jalisco, Mexico and photographed on Jan. 7, 2020.

The following detailed description sets forth the distinctive characteristics of 'FCM14-031'. The data which define these characteristics were collected from asexual reproductions of the original selection. Dimensions, sizes, colors, and other characteristics are approximations and averages set forth as accurately as possible. All measurements are the average of five observations. The plant history was taken on mature plants approximately 5 years of age, and the descriptions relate to plants grown in the field in Tala, state of Jalisco, Mexico unless otherwise noted. Descriptions of fruit characteristics were made on fruit grown in Tala, State of Jalisco, Mexico. Color designations are from "The Pantone Book of Color" (by Leatrice Eiseman and Lawrence Herbery, Harry N. Abrams, Inc., Publishers, New York 1990) unless noted otherwise. Where the Pantone color designations differ from the colors in the photographs, the Pantone colors are accurate.

VARIETY

Classification:
*Family*.—Ericaceae.
*Genus*.—*Vaccinium*.
*Species*.—*Corymbosum*.
*Common name*.—Southern Highbush Blueberry.

Parentage:
*Female parent*.—'FL00-180' (unpatented).
*Male parent*.—'FL01-06' (unpatented).

Market class: Commercial blueberry variety intended for the hand harvest fresh market.

PLANT

General:
*Parentage*.—'FL00-180' (female parent, unpatented) x 'FL01-06' (male parent, unpatented).
*Plant height*.—Average 144.6 cm.
*Plant width*.—139.6 cm.
*Growth habit*.—Round.
*Growth*.—Medium vigor.
*Productivity*.—High: amount of fruit produced per plant per season on average is 1.557 kg/plant for a one-year-old plant; 1.934 kg/plant for a two-years-old plant; 3.0172 kg/plant for a three-years-old plant; and 3.83 kg/plant for a four-years-old plant.
*Cold hardiness*.—Not determined, likely USDA zone 7 given southern highbush parentage.
*Chilling requirement*.—Zero.
*Leafing*.—Excellent leafing.
*Twigginess*.—Medium.
*Resistance/susceptibility to root rot* (*phytopthora cinnamomii*).—Does not appear to be overly susceptible.
*Resistance/susceptibility to stem blight* (*botryosphaeria sp.*).—Does not appear to be overly susceptible.
*Resistance/susceptibility to phomopsis twig blight* (*phomopsis vaccinii*).—Not evaluated.
*Resistance/susceptibility to botrytis* (*botrytis cinerea*).—Does not appear to be overly susceptible.
*Resistance/susceptibility to leaf spot* (*septoria spp.*).—Does not appear to be overly susceptible.

*Resistance/susceptibility to leaf rust* (*naohidemyces vaccinii*).—Good.
*Resistance/susceptibility to bud mites* (*acalatus vaccinii*).—Not evaluated.

FOLIAGE

General:
*Time of beginning of leaf bud burst*.—One to three weeks after prune.
*Leaf color* (*top side*).—Chive 19-0323.
*Leaf color* (*under side*).—Loden Green 18-0422.
*Leaf arrangement*.—Alternate and distichous.
*Leaf shape*.—Lanceolate.
*Leaf margins*.—Sinuate.
*Undulation of margins*.—Flat.
*Leaf venation*.—Anastomosing.
*Leaf apices*.—Attenuate.
*Leaf bases*.—Obtuse.
*Leaf length*.—Average of 61.5 mm.
*Leaf width*.—Average of 30.6 mm.
*Leaf length/width ratio*.—2.0 medium.
*Leaf nectaries*.—Absent.
*Pubescence of upper side*.—Absent.
*Pubescence of lower side*.—Absent.
*Cross sectional profile*.—Plane.
*Longitudinal profile*.—Entire.
*Attitude*.—Ascending.
*Fall foliage leaf color* (*top side*).—Chive 19-0323.
*Fall foliage leaf color* (*under side*).—Loden Green 18-0422.
Petioles:
*Length*.—6.12 mm.
*Width*.—4.3 mm.
*Color*.—Leek Green 15-0628.
*Surface texture*.—Smooth.

FLOWERS

General:
*Time of beginning of flowering*.—In Tala, Jalisco Mexico approximately 95-100 days after pruning (e.g., if prune in March, then flowering begins in August).
*Time of 50% anthesis*.—In Tala, Jalisco Mexico approximately 170-180 days after pruning.
*Flower shape*.—Urceolate.
*Flower bud density*.—Medium.
*Flower fragrance*.—Mild smell and sweet.
*Immature flower color*.—Frozen Dew 13-0513.
*Pollen staining*.—No data is available.
*Self-compatibility*.—Good, under control crosses, 84% of the fruit set when they were pollinated with the same variety pollen.
Corolla:
*Color*.—Bone White 12-0105.
*Length*.—11.46 mm.
*Width*.—7.01 mm.
*Aperture width*.—3.04 mm.
*Anthocyanin coloration of corolla*.—Absent at anthesis.
*Corolla ridges*.—Indistinct.
*Protrusion of stigma*.—Does not stick out.
Inflorescence:
*Length*.—75.69 mm.
*Diameter*.—30.79 mm.
*Length of peduncle*.—65.132 mm.
*Diameter of peduncle*.—1.44 mm.
*Surface texture of peduncle*.—Rough.
*Color of peduncle*.—Pompei 18-1426 and Apple Green 15-0543.
*Length of pedicel*.—11.204 mm.
*Diameter of pedicel*.—0.86 mm.
*Surface texture of pedicel*.—Soft.
*Color of pedicel*.—Pompei 18-1426 and Apple Green 15-0543.
*Number of flowers per cluster*.—10.2.
*Flower cluster density*.—High.
Calyx (with sepals):
*Diameter*.—5.734 mm.
*Color* (*sepals*).—Lettuce Green 13-0324.
*Calyx surface*.—Soft.
Stamen:
*Length*.—4.444 mm.
*Number per flower*.—9.8.
*Filament color*.—Adobe 17-1340.
Pistil:
*Length*.—10.01 mm.
*Ovary color* (*exterior*).—Green Oasis 15-0538.
*Style*.—Length — average of 5.246 mm.
Anther:
*Length*.—0.7 mm.
*Number*.—9.8.
*Color*.—Nugget 16-1148.
Pollen:
*Abundance*.—High.
*Color*.—Lemon Drop 12-0736.

FRUIT

General:
*Time of fruit ripening*.—In Tala, Jalisco Mexico approximately August 10$^{th}$ dependent on the time of previous pruning.
*Time of 50% maturity*.—In Tala, Jalisco Mexico approximately November 1 dependent on the time of previous pruning.
*Fruit development period*.—Approximately 65-75 days from fruit set to ripe.
*Mean harvest date*.—Approximately December 25 in Tala, Mexico when plants were pruned the previous June. Dependent on timing of previous pruning.
*Mean date last pick*.—Last pick occurred on approximately January 1 in Tala, Mexico. Dependent on timing of previous pruning.
*Cluster density*.—Medium.
*Berries per cluster*.—Average of 10.
*Unripe fruit color*.—Lettuce Green 13-0324.
*Ripe berry color*.—Lilae Gray 14-3903.
*Berry skin color after polishing*.—Patriot Blue 19-3925.
*Berry surface wax abundance*.—Medium.
*Berry flesh color*.—Died Moss 14-0626.
*Berry weight*.—3.08 g.
*Berry height from calyx to scar*.—16.44 mm.
*Berry diameter*.—21.154 mm.
*Calyx aperture*.—Average of 6.824 mm.
*Calyx depth*.—Average of 4.088 mm.
*Pedicel length*.—Average of 11.204 mm.
*Pedicel surface texture*.—Soft.
*Berry detachment force*.—Medium.

*Berry shape*.—Round.
*Fruit stem scar*.—Small.
*Berry flavor*.—Mild aromatic sub-acidic.
*Sweetness when ripe*.—Good, with brix average of 14.1.
*Firmness when ripe*.—Medium.
*Acidity when ripe*.—Medium.
*Storage quality*.—Good, 28-35 days at 2 degrees C.+/−2 degrees C.
*Suitability for mechanical harvesting*.—No information available.
*Self-fruitfulness*.—Good, control self-crossing showed a fruit set of 83%.
*Uses*.—Fresh market fruit production.

SEED

General:
*Seed abundance in fruit*.—5 average seeds per fruit.
*Seed color*.—Pecan Brown 17-1430.
*Seed dry weight*.—0.7 mg per one seed.
*Seed length*.—2.02 mm.

COMPARISON BETWEEN PARENTAL AND COMMERCIAL CULTIVARS

TABLE 1

Comparison Table

| Denomination of similar variety | Characteristic for comparison | State of expression of similar variety | State of expression of candidate variety ("FCM14-031") |
|---|---|---|---|
| "Biloxi" | Fruit: Size | Small to medium | Medium Large |
| "Biloxi" | Fruit: Color | Light blue | Medium Dark |
| "Biloxi" | Plant: Vigor | High | Medium |
| "FCM12-131" | Crop: Production Time | Early | Mid-Season |
| "FCM12-131" | Plant: Survival | Medium | High |

The invention claimed is:

1. A new and distinct variety of blueberry plant named 'FCM14-031', substantially as illustrated and described herein.

* * * * *